United States Patent [19]

Gray et al.

[11] Patent Number: 5,007,198

[45] Date of Patent: Apr. 16, 1991

[54] PROCESS FOR THE ACCELERATED PRODUCTION OF TRIPLOID SEEDS FOR SEEDLESS WATERMELON CULTIVARS

[75] Inventors: Dennis J. Gray, Howey-in-the-Hills; Gary W. Elmstrom, Leesburg, both of Fla.

[73] Assignee: University of Florida, Gainesville, Fla.

[21] Appl. No.: 204,158

[22] Filed: Jun. 8, 1988

[51] Int. Cl.$^5$ .......................... A01H 5/00; A01H 4/00; C12N 5/00

[52] U.S. Cl. ................................ 47/58; 47/DIG. 1; 800/255; 800/DIG. 18; 800/DIG. 19; 435/240.5; 435/240.51

[58] Field of Search .............................. 800/1; 47/58; 435/240.5

[56] References Cited

PUBLICATIONS

Wall, J. R. (1960), "Use of Marker Genes in Producing Triploid Watermelons", Am. Soc. Hort. Sci., 76:577–588.

Barnes, L. R., F. D. Cochran, R. L. Mott and W. R. Henderson (1978), "Potential Uses of Micropropagation for Cucurbits", Cucurbit Growers Coop., 1:21–22.

Anghel, I., and A. Rosu (1985), "In Vitro Morphogenesis in Diploid, Triploid and Tetraploid Genotypes of Watermelon–*Citrullus lanatus* (Thumb.), Mansf., ", Rev. Roumaine de Biologie, Biologie Vegetale 30:43–55.

Handley et al., (1979), Hort. Science 14(1): 22–23.

Mohr (1986), In, Breeding Vegetable Crops., Ed. Bassett, M., The AVI Publishing Company Inc., Westport, Conn., pp. 37–66.

*Primary Examiner*—Howard J. Locker
*Assistant Examiner*—Gary Benzion
*Attorney, Agent, or Firm*—Saliwanchik & Saliwanchik

[57] ABSTRACT

Disclosed here is a novel process which facilitates the rapid and economical production of seedless watermelon seed. The novel process involves cloning desirable tetraploid watermelon parental lines. These parental lines are essential in the production of triploid seed for the seedless watermelon. The subject invention makes possible the use of self-sterile tetraploid parental lines in the production of triploid seed.

9 Claims, No Drawings

PROCESS FOR THE ACCELERATED PRODUCTION OF TRIPLOID SEEDS FOR SEEDLESS WATERMELON CULTIVARS

BACKGROUND OF THE INVENTION

During 1981, the last year for which nationwide records are available, 82,460 hectares with a production value of $159,300,000.00 were devoted to watermelon in the United States alone. Of these, 19,800 hectares (value $52,700,000.000) were in Florida. Records for Florida in 1984 indicate that 24,300 hectares were planted with a value of $62,100,000.00. In addition, watermelon is a major crop in other regions of the world.

Of all watermelon cultivars, those with seedless fruit are the most desirable and bring the highest prices. Seedless fruit, in general, receives greater consumer acceptance and demand. For example, the recent release of a single seedless grape cultivar 'Red Flame' was responsible for a jump from 10th to 4th in consumer fresh fruit preference for grapes and stimulated an explosion of new acreage. Although seedless watermelon cultivars have been available for several years, technical difficulties in producing seed have kept the availability of planting stock low and the price of seed prohibitively high. Additionally, much variation in quality occurs between seedless watermelons.

The seedless condition in watermelon is almost always the result of the presence of three homologous complements per cell rather than the usual two. Cells with three homologous chromosomes are said to be triploid and are designated as 3x. The inability of the triploid zygote to develop normally into an embryo causes the absence of seeds in triploid plants. The abnormal embryo formation causes cessation of normal ovular development into a seed at an early stage. Typically, seedless watermelons contain small edible white ovules, similar to those in immature cucumbers.

Triploid seeds are produced by crossing diploid (2x) lines containing 22 chromosomes per cell with tetraploid (4x) lines containing 44 chromosomes per cell. This results in seeds that produce triploid (3x) plants with 33 chromosomes. Triploid plants are true $F_1$ hybrids so their production depends on development of diploid and tetraploid parental lines (Wall [1960] Am. Soc. Hort. Sci. 76:577-588).

For large-scale commercial production of triploid seed, tetraploid and diploid parental lines are planted in mixed plots and allowed to cross pollinate. Triploid seed is produced only in melons on tetraploid plants that are fertilized with diploid pollen. Therefore, an adequate supply of diploid and tetraploid seed must be available to produce large mixed stands. All commercially grown seeded watermelons are diploid; therefore, lines for use as diploid parents are abundant. The major limitation to producing seedless watermelon lies in the difficulty associated with producing sufficient seed for the tetraploid (4x) parental lines which are eventually pollinated with a diploid (2x) to produce the seedless triploid (3x) seed.

Tetraploid lines are produced from diploid seedlings by application of colchicine. With either diploid or tetraploids, once a desirable cultivar is identified, the plant is self-pollinated in order to build up adequate seed. Diploid seed is easily produced by open pollination of pure stands of a given diploid cultivar. Tetraploid seed, however, has proven to be very difficult to produce in large, commercially useful, quantities. This is largely due to the fact that tetraploids exhibit a high degree of self-sterility. As a result of this self-sterility, very few melons develop in a field of tetraploid plants. Also, none or only a small number of seeds are usually produced in each self-pollinated melon. A productive cross will yield only 50-100 seeds per fruit. Therefore, ten or more years are typically required to increase seed of a new tetraploid line to commercially acceptable numbers.

This extremely slow accumulation of parental seed has been a major roadblock to the commercial production of triploid seed for seedless watermelon. In fact, this roadblock has been of such magnitude as to squelch development of a substantial seedless watermelon industry. For instance, triploid seedless watermelon seed now costs from $220.00 per pound to $600.00 per pound compared to $91.00 per pound for diploid hybrids and $10.00 per pound for popular open pollinated varieties. Overcoming the difficulty in producing seedless watermelon would revolutionize the watermelon industry. The invention disclosed here alleviates major technical difficulties in triploid seed production.

In addition to the inability to produce sufficient quantities of tetraploid parental seeds of acceptable quality, seedless watermelon farmers are constantly at risk of having their few high quality tetraploid strains become available to competitors. This can happen because, in a field of diploid and tetraploid plants, some of the tetraploid plants will self pollinate rather than be cross-pollinated by the diploid plants. Of course, cross-pollination results in fruit containing the desired triploid seed. Self-pollination of the tetraploid, however, results in a melon bearing the tetraploid seed. These melons with tetraploid seed are physically indistinguishable from the melons with the triploid seed. Therefore, 4x seed becomes mixed with 3x seed during seed production and this mixed seed is often sold to growers. Also it is possible that the same melon can contain both 3x and 4x seed. This can happen when one tetraploid flower is pollinated with pollen from both a 2x and a 4x plant.

As a result, the grower often obtains a mixed stand of 4x and 3x melons. For example, these melons are physically distinguishable from each other. The tetraploid melons are can be striped but the triploid melons can be plain. Usually growers sell the 4x melon at a much reduced price as a lower quality seeded variety. Consequently, the seeds for the desired, and difficult to produce, tetraploid line are made available to the public.

The invention disclosed here allows seed producers to rapidly produce tetraploid parental plants, while minimizing or eliminating the possibility of the production of unwanted tetraploid melons.

One step in the claimed process involves cloning tissue cultures of the tetraploid parental line. The few previous cloning efforts with respect to watermelons have primarily concentrated on the feasibility of cloning diploid and triploid cultivars. This prior research was done with the hope that the triploid plants could be successfully cloned and sold as viable transplants to farmers (Barnes et al. [1978] Cucurbit Growers Coop. 1:21-22; Barnes [1979] Sci. Hort. 11:223-227; Anghel and Rosu [1985] Rev. Roumaine de Biologie, Biologie Vegetale 30:43-55). However, these efforts have not successfully resulted in a method of commercially producing the seedless triploid cultivar. Also, plant growth and fruiting performance in the field has not been documented. Furthermore, previous researchers have not suggested ways to overcome problems associated with the destruction of the early growth phases as a result of misting. Misting was believed by some to be necessary to provide an intermediate environment between culture and the field in order to acclimate plants. Using modified cloning procedures as part of a novel process for producing tetraploidal parent strains, the disclosed invention overcomes the major obstacles which have prevented the development of the seedless watermelon industry. Also, by using cloned tetraploids it is possible to produce more uniform seedless melons. The disclosed process facilitates the rapid increase of tetraploid lines without the need for self-pollination.

BRIEF SUMMARY OF THE INVENTION

The disclosed invention is a process whereby rapid increase of tetraploid parental lines is made possible for the first time. This novel process overcomes the major obstacle of tetraploid self-sterility which caused the production and accumulation of triploid seeds to proceed extremely slowly. Specifically, the claimed invention involves the following steps:

(1) Produce and identify a suitable tetraploid parental cultivar.
(2) Clone the cultivar using unique tissue culture techniques.
(3) Transplant and grow the new plants in a suitable soil medium.
(4) Plant the tetraploid plants in a field or greenhouse in a mixed stand with diploid plants.
(5) Collect the triploid seed from the fruit produced when the tetraploid plants are pollinated by the diploid plants.

Advantageously, it is not necessary for the tetraploid parent cultivar to be capable of self-pollination. Therefore, it is possible to select appropriate parent lines on the basis of characteristics which have significance to the consumer without regard to characteristics related to self-sterility.

Also, the disclosed invention makes it possible to purposely use tetraploid parent lines which are self-sterile. The use of self-sterile lines eliminates the possibility of inadvertently producing tetraploid seed during the triploid seed production stage. Outside the context of producing seed, tetraploid watermelons are undesirable because they have seeds, are less attractive to the consumer, and provide competitors with an opportunity to obtain seeds for desirable cultivars.

DETAILED DESCRIPTION OF THE INVENTION

The hindrance of tetraploid self-sterility has been overcome by developing a process for rapidly increasing tetraploid parental lines without conventional breeding. This process has the potential for production of 4–5 million plants from a single elite plant in 6 months. This figure greatly exceeds the number of tetraploid plants required for production of seedless watermelon cultivars. Whether or not the tetraploid line is self-sterile is inconsequential. This new methodology promises to decrease development time for seedless cultivars from 10 or more years to approximately one year. The first step in the disclosed novel process is to identify a suitable tetraploid parental cultivar. Because the tetraploid cultivar occurs very infrequently in nature, it is necessary to induce the formation of this unusual condition. The primary means for inducing this abnormality is through applying colchicine to young diploid plants or to seeds.

Colchicine inhibits mitotic spindle formation and this leads to cells with various chromosome numbers. Tetraploids can be successfully produced by applying one drop per day of 0.2 to 0.4 percent aqueous colchicine to diploid seedling apices. This treatment with colchicine may result in the death of the seedling or seed, or it can produce aneuploids (cells with extra or missing chromosomes) or polyploids. Polyploids are cells with complete duplicate sets of chromosomes. Examples of polyploids resulting from colchicine treatments are: tetraploids (4x), hexaploids (6x), and octaploids (8x). Tetraploid plants that result from colchicine treatment are identified based on cytological examination and seed shape of fruiting plants. Generally, tetraploid seed is larger and more irregular in shape when compared to diploid seed. Additionally, tetraploid plants are more robust than diploid plants.

Mother plants (that is, the plants which are used for the cloning) can be at any stage of growth from seedling through flowering and fruiting. Plants from the greenhouse or field can be used. However, field-grown plants can be used advantageously in order to select for superior field performance. By using field crops, cultivars can be selected on the basis of hardiness and fruit characteristics and any other factor that the grower deems to be relevant. Also it is possible to select tetraploid plants which are self-sterile. This practice is the exact opposite of current techniques which necessitate the use of cultivars which are not self-sterile. The primary advantage of using self-sterile plants is that these plants will only produce the desired seedless triploid melon, not seeded tetraploids, when they are planted in the mixed stands of diploids and tetraploids. Additionally, in searching for suitable tetraploid parentals, self-sterile varieties are much more common than self-fertile lines. Ability to not exclude self-sterile lines allows much more latitude in selecting parentals with outstanding agronomic characteristics.

Thus the disclosed process has the distinct advantages of accelerating the development of improved seedless cultivars as well as reducing the odds of growing tetraploid fruit which is less desirable to the consumer and presents competitors with the opportunity to obtain valuable seeds for the cost of a watermelon.

Once suitable tetraploids are identified, the plants are cloned in order to greatly increase their numbers. For culture initiation, tissue is taken directly from shoot or axillary bud apical meristems of growing plants. For example, shoot-tips can be surface sterilized for 3 minutes in a 25% solution of commercial bleach, rinsed in sterile water, and the apical meristems micro-dissected. Apical meristems are placed on a solidified culture medium with growth regulators that encourage adventitious buds to form. Examples of appropriate growth regulators include cytokinins such as kinetin (K) or benzyladenine (BA).

The medium itself can consist of Murashige and Skoogs' salts and vitamins (Murashige, T. and F.M. Skoog, [1962] "A Revised Medium for Rapid Growth and Bioassays with Tobacco Tissue Cultures," Physiologia Plantarium 15:473–497) plus 3% sucrose, 1 mg/l BA and 0.7% agar. On this medium, each apical meristem proliferates into a mass of tissue containing numerous adventitious buds.

After four weeks, cultures are transferred to fresh shoot elongation medium. This medium can consist of the same salt, vitamin, sugar and agar concentration as the initial culture medium. Added to the medium is about 8 mg/l indoleacetic acid (IAA) with about 2 mg/l K. Alternatively, naphthalene acetic acid (NAA) can be substituted for IAA and BA can be substituted for K.

Numerous shoots grow from each original apical meristem. An average of seven shoots per apex are obtained in some lines but as few as only one shoot per apex are obtained in other lines. Therefore the ability to proliferate shoots in culture appears to be genotype dependent.

For culture increase, tissue masses on bud initiation medium are subdivided into several pieces every four weeks and transferred to fresh medium. Each original meristem is thereby induced to form a nearly unlimited number of buds. Cultures can be maintained and increased in this manner for over two years.

When a monthly proliferation rate of five shoots per apex is obtained for 20 original apices, over 1,560,000 shoots can result in seven months of recurrent subculture. For plant recovery, shoots approximately 2 cm long are cut and placed in rooting medium. This rooting medium consists of approximately ½ the concentration of the salts, vitamins and sucrose and the same amount of agar as above. However, about 8 mg/l IAA or NAA are used.

When roots appear, the plantlets are acclimated in soil in a humid covered chamber and kept for one week under artificial lights. The plants are not subjected to misting because we have determined that tissue culture-derived watermelon plants under mist absorb an excess of water which leads to death. In contrast, plants maintained in a humid chamber acclimate well and high recovery rates are achieved.

After one week in the humid covered chamber under artificial lights, the chamber is then placed in a greenhouse. When new shoot growth is observed, the lid is gradually removed during the course of one week. The resulting plants are then transplanted to the field.

Subsequent maintenance procedures are identical to those used for seedling plants. These plants can be directly planted in a field with diploid plants in order to create the mixed stands necessary for the production of the triploid seed. Alternatively, the plantlets of self-fertile lines can be grown and the seed collected from the tetraploid fruit. This seed would then subsequently be planted in the mixed stands of diploid and tetraploid plants.

Once the mixed stands are planted, the fruit containing the desired triploid seed forms on tetraploid plants which have been pollinated by diploid plants. The seed producer collects this seed and sells it to growers. Where the tetraploid cultivar has been chosen to be self-sterile, no fruit containing tetraploid seed will develop. Therefore, the seed which is collected and sold to growers will be of particularly high quality because no seeded melons will develop. Also, because no seeded watermelons will develop, the seed producer does not have to be concerned about the transfer to competitors of valuable tetraploid cultivar seed.

We claim:

1. A process for producing triploid seed for seedless watermelons, said process comprising the following steps:
   i. Producing and identifying a suitable tetraploid parental cultivar;
   ii. Cloning the tetraploid parental cultivar using in vitro tissue culture techniques;
   iii. Transplanting and growing the new plants in a suitable soil medium;
   iv. Planting the tetraploid plants in a field or greenhouse in a mixed stand with diploid plants; and
   v. Collecting the triploid seed from the fruit produced when the tetraploid plants are pollinated by the diploid plants.

2. A process, according to claim 1, wherein said tetraploid parental lines are self-sterile.

3. A process, according to claim 2, wherein cloned plantlets are kept in humid conditions but are not subjected to misting.

4. A process, according to claim 1, where the cloning of said tetraploidal parental lines comprises the following steps: taking tissue directly from the shoot or axillary bud apical meristems of growing plants; placing said tissue on a solidified culture medium, said medium containing growth regulators that encourage adventitious buds to form; after about 4 weeks, transferring cultures to shoot elongation medium; placing shoots of approximately 2 cm in length in rooting medium; after the appearance of roots, acclimating the plantlets in soil in a humid covered chamber under artificial lights for about one week; once new shoot growth is observed, gradually removing the lid over the course of about a week, and transplanting the resulting plants to the field.

5. A process, according to claim 4, wherein said growth regulators are cytokinins.

6. A process, according to claim 4, wherein said growth regulators are kinetin, benzyladenine, or a combination of the two.

7. A process, according to claim 4, wherein said solidified culture medium comprises Murashige and Skoogs' salts and vitamins, plus 3% sucrose, 1 mg/l benzyladenine and 0.7% agar.

8. A process, according to claim 4, wherein said shoot elongation medium comprises Murashige and Skoogs' salts and vitamins, plus 3% sugar, 0.7% agar together with:
   (a) indoleacetic acid or naphthalene acetic acid; and
   (b) kinetin or benzyladenine.

9. A process, according to claim 4, wherein said medium has about 8 mg/l indoleacetic acid and about 2 mg/l kinetin.

* * * * *

UNITED STATES PATENT AND TRADEMARK OFFICE
CERTIFICATE OF CORRECTION

PATENT NO. : 5,007,198

DATED : April 16, 1991

INVENTOR(S) : Dennis J. Gray, Gary W. Elmstrom

It is certified that error appears in the above-identified patent and that said Letters Patent is hereby corrected as shown below:

| | |
|---|---|
| Column 1: | line 31: "complements per cell" should read --chromosome complements per cell--. |
| Column 2: | line 46: "are can be striped" should read --can be striped--. |
| Column 6, claim 3, | line 1: "claim 2" should read --claim 1--. |

Signed and Sealed this

Twenty-second Day of September, 1992

Attest:

DOUGLAS B. COMER

Attesting Officer     Acting Commissioner of Patents and Trademarks